(12) United States Patent
Zuk, Jr.

(10) Patent No.: US 7,798,333 B2
(45) Date of Patent: Sep. 21, 2010

(54) SYSTEMS, APPARATUS AND METHODS FOR VACUUM FILTRATION

(75) Inventor: Peter Zuk, Jr., Harvard, MA (US)

(73) Assignee: Roush Life Sciences, LLC, Livonia, MI (US)

(*) Notice: Subject to any disclaimer, the term of this patent is extended or adjusted under 35 U.S.C. 154(b) by 206 days.

(21) Appl. No.: 11/516,011

(22) Filed: Sep. 5, 2006

(65) Prior Publication Data

US 2007/0144959 A1 Jun. 28, 2007

Related U.S. Application Data

(60) Provisional application No. 60/714,017, filed on Sep. 2, 2005.

(51) Int. Cl.
*B01D 29/085* (2006.01)

(52) U.S. Cl. .............. 210/406; 422/101; 422/104; 248/94; 248/154; 210/416.1; 210/473

(58) Field of Classification Search .............. 422/101, 422/102, 104, 103; 248/94, 154; 210/406, 210/248, 250, 416.1, 241, 473, 474, 455; 435/308.1
See application file for complete search history.

(56) References Cited

U.S. PATENT DOCUMENTS

| | | | | |
|---|---|---|---|---|
| 1,168,988 A | * | 1/1916 | Zimmermann | 99/292 |
| 1,216,112 A | | 2/1917 | Greven | 210/477 |
| 1,501,073 A | | 7/1924 | Stead | 210/478 |
| 2,460,423 A | | 2/1949 | Kracklauer | 210/479 |
| 2,584,206 A | | 2/1952 | Hodsdon | 210/445 |
| 2,608,843 A | * | 9/1952 | Kennedy | 141/340 |
| 2,818,178 A | | 12/1957 | Hodsdon | 210/445 |
| 3,010,583 A | | 10/1959 | Kenyon | 210/406 |
| 3,319,792 A | * | 5/1967 | Leder et al. | 210/238 |
| 3,469,369 A | | 9/1969 | Helmke | 95/259 |
| 3,478,889 A | | 11/1969 | Fessler | 210/406 |

(Continued)

FOREIGN PATENT DOCUMENTS

EP 0 857 961 A2 8/1988

(Continued)

OTHER PUBLICATIONS

Authorized Officer Arnaldo de Biasio, *International Search Report and Written Opinion of the International Searching Authority*, International Application No. PCT/US2006/034560, Jan. 18, 2007, 11 pages.

*Primary Examiner*—Terry K Cecil
(74) *Attorney, Agent, or Firm*—Sunstein Kann Murphy & Timbers LLP

(57) ABSTRACT

A liquid filtering system and methods for filtering are disclosed. One embodiment of the system includes a filtering apparatus having a receiving receptacle coupled with an adapter. The adapter has an adapter port for receiving a vacuum and an interface for coupling with an output receptacle that receives filtered liquid from the filtering apparatus. The adapter is between the receiving receptacle and output receptacle when the output receptacle is coupled with the adapter interface. The system also includes a base having a substantially rigid housing containing an internal vacuum channel terminating at a base vacuum delivery port. The adapter is couplable with the base to connect the adapter port to the base vacuum delivery port.

38 Claims, 12 Drawing Sheets

U.S. PATENT DOCUMENTS

| | | | |
|---|---|---|---|
| 3,730,352 A | 5/1973 | Cohen et al. | 210/332 |
| 3,752,651 A * | 8/1973 | Bush | 436/177 |
| 3,838,978 A | 10/1974 | Eddleman et al. | 23/292 |
| 3,956,125 A | 5/1976 | Strutt et al. | 210/94 |
| 4,052,163 A | 10/1977 | Patzner | 23/259 |
| 4,247,399 A | 1/1981 | Pitesky | 210/341 |
| 4,251,366 A * | 2/1981 | Simon et al. | 210/767 |
| 4,301,010 A | 11/1981 | Eddleman et al. | 210/406 |
| 4,357,240 A | 11/1982 | Mehra et al. | 210/455 |
| 4,394,266 A | 7/1983 | Mehra et al. | 210/244 |
| 4,521,308 A * | 6/1985 | Brimhall et al. | 210/330 |
| 4,523,934 A | 6/1985 | Joshua | 55/189 |
| 4,614,585 A | 9/1986 | Mehra et al. | 210/433.2 |
| 4,673,501 A | 6/1987 | Wells et al. | 210/406 |
| 4,678,572 A | 7/1987 | Hehl | 210/232 |
| 4,678,576 A | 7/1987 | Leoncavallo | 210/433.2 |
| 4,689,147 A | 8/1987 | Leoncavallo et al. | 210/232 |
| 4,702,834 A | 10/1987 | Relyea | 210/321.78 |
| D297,860 S | 9/1988 | Leoncavallo et al. | D24/8 |
| 4,783,318 A | 11/1988 | Lapakko | 422/101 |
| 4,792,398 A | 12/1988 | Klein | 210/406 |
| 4,849,061 A | 7/1989 | Relyea | 156/308.4 |
| 4,894,155 A | 1/1990 | Leoncavallo et al. | 210/321.84 |
| 4,944,876 A | 7/1990 | Miller | 210/321.75 |
| 5,112,484 A | 5/1992 | Zuk, Jr. | 210/247 |
| 5,116,496 A | 5/1992 | Scott | 210/232 |
| 5,141,639 A | 8/1992 | Kraus et al. | 210/321.75 |
| 5,205,989 A | 4/1993 | Aysta | 422/101 |
| 5,227,137 A | 7/1993 | Monti et al. | 422/101 |
| 5,234,585 A | 8/1993 | Zuk, Jr. | 210/188 |
| 5,264,184 A | 11/1993 | Aysta | 422/101 |
| 5,283,039 A | 2/1994 | Aysta | 422/104 |
| 5,308,483 A | 5/1994 | Sklar et al. | 210/232 |
| 5,375,477 A | 12/1994 | Neill et al. | 73/863.23 |
| 5,447,079 A | 9/1995 | Neill et al. | 73/863.23 |
| 5,603,900 A | 2/1997 | Clark et al. | 422/101 |
| 5,785,927 A | 7/1998 | Scott et al. | 422/104 |
| 5,792,425 A | 8/1998 | Clark et al. | 422/101 |
| 5,873,967 A | 2/1999 | Clark et al. | 156/70 |
| 5,948,246 A | 9/1999 | Zuk, Jr. | 210/188 |
| 6,159,368 A | 12/2000 | Moring et al. | 210/321.75 |
| 6,338,802 B1 | 1/2002 | Bodner et al. | 210/650 |
| 6,358,730 B1 | 3/2002 | Kane | 435/297.5 |
| 6,379,625 B1 | 4/2002 | Zuk, Jr. | 422/101 |
| 6,419,827 B1 | 7/2002 | Sandell et al. | 210/321.75 |
| 6,443,314 B2 | 9/2002 | Shiraiwa et al. | 210/474 |
| 6,451,261 B1 | 9/2002 | Bodner et al. | 422/99 |
| 6,458,278 B1 | 10/2002 | Leoncavallo et al. | 210/650 |
| 6,491,873 B2 | 12/2002 | Roberts et al. | 422/101 |
| 6,506,343 B1 | 1/2003 | Bodner et al. | 422/65 |
| 6,770,203 B2 | 8/2004 | Leoncavallo et al. | 210/650 |
| 6,783,732 B2 | 8/2004 | Madden et al. | 422/63 |
| 6,913,152 B2 | 7/2005 | Zuk, Jr. | 210/406 |
| 6,951,762 B2 | 10/2005 | Zuk, Jr. | 436/180 |
| 6,986,849 B2 | 1/2006 | Irvine | 210/791 |
| 7,011,755 B2 | 3/2006 | Zuk, Jr. | 210/416.1 |
| 2002/0096468 A1 | 7/2002 | Zuk, Jr. | 210/455 |
| 2003/0010708 A1 | 1/2003 | Leocavallo et al. | 210/477 |
| 2003/0080045 A1 | 5/2003 | Zuk, Jr. | 210/416.1 |
| 2005/0178216 A1 | 8/2005 | Pitt et al. | 73/863.23 |

FOREIGN PATENT DOCUMENTS

| | | |
|---|---|---|
| GB | 2 250 927 | 6/1992 |
| WO | WO 93/12853 | 7/1993 |
| WO | WO 95/04585 | 2/1995 |

* cited by examiner

SYSTEMS, APPARATUS AND METHODS FOR VACUUM FILTRATION

CROSS REFERENCE TO RELATED APPLICATIONS

This application claims priority to U.S. Provisional Patent Application Ser. No. 60/714,017, filed Sep. 2, 2005, which is incorporated herein by reference in its entirety.

TECHNICAL FIELD AND BACKGROUND ART

This invention relates to the filtration field, and more particularly, to a disposable vacuum filtration device and reusable apparatus capable of filtering liquid samples.

Many disposable vacuum filtration devices for filtering liquid samples are available today. The currently available disposable vacuum filtration devices for filtering liquid samples may include a receptacle for collecting the filtered liquid, a removable funnel section that contains a filter element, a removable lid that caps the top of the funnel section, and a cap for the receiving container to cap the container after the funnel section has been removed. The funnel section contains a filter support that provides support for the filter element and provides fluid flow communication between the downstream side of the filter element and the interior of the receptacle. The funnel section also contains a vacuum port, and a way to apply a vacuum to the interior of the receptacle. The outer periphery of the filter element is sealed to the device to prevent un-filtered liquid from entering the receptacle. The removable lid is press fitted onto the top of the removable funnel section typically with a fit that allows easy removal, but does not allow the lid to accidentally separate from the funnel section. These devices are normally sold pre-sterilized.

In use, the end user removes a sterile vacuum filtration device from its shipping package in a laminar flow hood to prevent contaminating the device. The lid is then removed from the funnel section and a liquid sample to be filtered is poured into the funnel section. The lid is then placed back onto the funnel section and the vacuum port of the funnel section is connected to a vacuum source. The vacuum source pulls the liquid through the filter element and into the receptacle. Either the lid or the funnel section may contain venting to allow air to replace the liquid in the funnel as the vacuum removes the liquid from the funnel.

After all of the liquid sample has been pulled into the receptacle, the user removes the funnel section from the receptacle and places the cap onto the receptacle to keep the contents sterile. The funnel section may then be discarded.

SUMMARY OF THE INVENTION

One embodiment of the present invention is directed to a liquid filtering system. The system of this embodiment includes a filtering apparatus having a receiving receptacle coupled with an adapter. The adapter has an adapter port for receiving a vacuum and an interface for coupling with an output receptacle for receiving filtered liquid from the filtering apparatus. The adapter is between the receiving receptacle and output receptacle when the output receptacle is coupled with the adapter interface. The system also includes a base having a substantially rigid housing containing an internal vacuum channel terminating at a base vacuum delivery port. In this embodiment, the adapter is couplable with the base to connect the adapter port to the base vacuum delivery port.

One aspect of this embodiment includes a cell culture medium filter for filtering a liquid received by the receiving receptacle.

In another aspect of this embodiment, when the output receptacle is coupled with the adapter interface, the base suspends the output receptacle above a bottom portion of the base to form a gap therebetween.

In another aspect of this embodiment, the housing defines the vacuum channel.

Another embodiment of the present invention is directed to a liquid filtering system. The system of this embodiment includes a filtering apparatus having a receiving receptacle coupled with an adapter and an output receptacle for receiving filtered liquid from the filtering apparatus. The system of this embodiment also includes a substantially rigid base couplable with the adapter and a vacuum channel in fluid communication with the output receptacle. In this embodiment, the base suspends the output receptacle.

In one aspect of this embodiment, the base has a bottom portion and the output receptacle is spaced from the bottom portion.

In another aspect of this embodiment the vacuum channel is contained substantially entirely within the base and connects with the adapter to provide a vacuum.

Another embodiment of the present invention is directed to a liquid filtering system. The system of this embodiment includes a filtering apparatus having a receiving receptacle coupled with an adapter and a substantially rigid base having a vacuum channel. The base in this embodiment is removably couplable with the filtering apparatus. In this embodiment, the filtering apparatus and the base have corresponding registration details for orienting the adapter in a manner that that connects the vacuum channel with the adapter.

Another embodiment of the present invention is directed to filtering assembly for use with a substantially rigid base having a base vacuum channel, The assembly of this embodiment includes a receiving receptacle and an adapter coupled with the receiving receptacle. The adapter of this embodiment includes an adaptor port, is removably couplable with the base, and has a first registration detail for orienting the adapter in a manner that connects the base vacuum channel with the adapter port.

Another embodiment of the present invention is directed to a support base for supporting a filtering apparatus coupled with an output receptacle. In this embodiment, the filtering apparatus has a port for receiving a vacuum. The support base of this embodiment includes a substantially rigid housing containing a vacuum channel and a support for supporting the filtering apparatus. In this embodiment, at least one of the housing and support having a base registration detail for orienting the filtering apparatus in a manner that connects the base vacuum channel with the filtering apparatus port. In this embodiment, the support is upstream of the output receptacle when supporting the filtering apparatus.

Another embodiment of the present invention is directed to a support base for supporting a filtering apparatus coupled with an output receptacle. In this embodiment the filtering apparatus has a port for receiving a vacuum. The support base of this embodiment includes a substantially rigid housing that substantially entirely contains a vacuum channel and a support for removably coupling with the filtering apparatus. In this embodiment, the vacuum channel is connected to the filtering apparatus port when the support couples with the filtering apparatus. In this embodiment the support is upstream of at least a portion of the output receptacle when the support couples with the filtering apparatus.

Another embodiment of the present invention is directed to a method of filtering a cell culture medium. The method of this embodiment includes providing a filtering apparatus having a filter that is capable of appropriately filtering the cell culture medium. The filtering apparatus of this embodiment has a filtering apparatus port for receiving a vacuum and is coupled with an output receptacle. The method of this embodiment also includes coupling the filtering apparatus to a portion of a base, the base having a vacuum channel, the filtering apparatus fitting in registry with corresponding registry details of the base to orient the filtering apparatus port with the vacuum channel in the base; and applying a vacuum to the interior of the output receptacle through the vacuum channel and the filtering apparatus. The method of this embodiment also includes pouring the cell culture medium into the filtering apparatus; permitting the given cell culture medium to pass through the filtering apparatus to the output receptacle downstream of the portion of the base coupled with the filtering apparatus; removing the output receptacle from the filtering apparatus; and uncoupling the filtering apparatus from the base.

Another embodiment of the present invention is directed to a liquid filtering system that includes a filtering apparatus, an output receptacle removably coupled with the filtering apparatus and a substantially rigid base. The base of this embodiment includes a vacuum channel and a coupling portion that is removably couplable with the filtering apparatus to provide a vacuum to the output receptacle. In this embodiment, the coupling portion of the base is upstream of at least a portion of the output receptacle.

Another embodiment of the present invention is directed to a method of filtering a liquid sample including providing a filtering apparatus having a filter that is capable of appropriately filtering the liquid sample, the filtering apparatus having a filtering apparatus port for receiving a vacuum and being coupled with an output receptacle; coupling the filtering apparatus to a portion of a base, the base having a vacuum channel, the filtering apparatus oriented on the base such that filtering apparatus port is in fluid communication with the vacuum channel in the base; applying a vacuum to the interior of the output receptacle through the vacuum channel and the filtering apparatus; pouring the liquid sample into the filtering apparatus; permitting the liquid sample to pass through the filtering apparatus to the output receptacle downstream of the portion of the base coupled with the filtering apparatus; removing the output receptacle from the filtering apparatus; and uncoupling the filtering apparatus from the base.

Another embodiment of the present invention is directed to a vacuum filtration apparatus including a disposable filtration device. The filtration device of this embodiment includes a disposable filtration funnel capable of holding un-filtered liquid therein, a receptacle disposed below said funnel, said receptacle including a single opening located at the top of said receptacle, a filter disposed between the un-filtered liquid and the top of the disposable receptacle, with said filtered sealed to said filtration device to prevent the flow of un-filtered liquid into said receptacle, and an inlet that is not a part of the receptacle, in fluid flow communication with said opening of said receptacle. The apparatus also includes a reusable base releasably supporting said vacuum filtration device, and having an opening through which vacuum may be applied to said base, with the vacuum of said base being automatically applied to said inlet of said disposable filtration device when the disposable filtration device is placed onto the reusable base, thereby drawing liquid from said funnel, through said filter, into said filtration receptacle.

Another embodiment of the present invention is directed to a vacuum filtration apparatus including a disposable filtration device that includes a disposable filtration funnel capable of holding un-filtered liquid, a disposable receptacle disposed below said funnel, said receptacle including a single opening located at the top of said receptacle, a filter disposed between the un-filtered liquid and the top of the disposable receptacle, with said filtered sealed with a non-releasable seal to said filtration device to prevent the flow of un-filtered liquid into said receptacle. The apparatus of this embodiment includes a reusable base releasably supporting said vacuum filtration device, and having an opening through which vacuum may be applied to said base. The reusable base is operatively connected to the interior of said filtration receptacle so that the vacuum of said base may be applied to said filtration receptacle to draw liquid from said funnel, through said filter, into said filtration receptacle.

Another embodiment of the present invention is directed to a vacuum filtration apparatus that includes a disposable filtration device which includes a disposable filtration funnel capable of holding un-filtered liquid, a receptacle disposed below said funnel, said receptacle including a single opening located at the top of said receptacle, with the receptacle releasably attached to the funnel, and a filter disposed between the un-filtered liquid and the top of the disposable receptacle, with said filtered sealed to said filtration device to prevent the flow of un-filtered liquid into said receptacle. The apparatus also includes a reusable base releasably supporting said vacuum filtration device, and having an opening through which vacuum may be applied to said base that is operatively connected to the interior of said filtration receptacle so that the vacuum of said base may be applied to said filtration receptacle to draw liquid from said funnel, through said filter, into said filtration receptacle, when said disposable filtration device is placed onto said reusable base.

Another embodiment of the present invention is directed to a vacuum filtration apparatus that includes a disposable filtration device which includes a disposable filtration funnel capable of holding un-filtered liquid, a receptacle disposed below said funnel, said receptacle including a single opening located at the top of said receptacle, with the receptacle releasably attached to the funnel, and a filter disposed between the un-filtered liquid and the top of the disposable receptacle, with said filtered sealed to said filtration device to prevent the flow of un-filtered liquid into said receptacle. The apparatus also includes a reusable base releasably supporting said vacuum filtration device, and having an opening through which vacuum may be applied to said base. The base is automatically connected to the interior of said filtration receptacle so that the vacuum of said base may be applied to said filtration receptacle to draw liquid from said funnel, through said filter, into said filtration receptacle, when said disposable filtration device is placed onto said reusable base.

Another embodiment of the present invention is directed to a vacuum filtration apparatus which includes a disposable filtration device that includes a disposable filtration funnel capable of holding un-filtered liquid, a disposable receptacle disposed below said funnel, said receptacle including a single opening located at the top of said receptacle, and a filter disposed between the un-filtered liquid and the top of the disposable receptacle, with said filtered sealed to said filtration device to prevent the flow of un-filtered liquid into said receptacle. The apparatus also includes a reusable base releasably supporting said vacuum filtration device, and having an opening through which vacuum may be applied to said base, wherein the reusable base is operatively connected to the interior of said filtration receptacle so that the vacuum of said base may be applied to said filtration receptacle to draw liquid from said funnel, through said filter, into said filtration receptacle, and wherein said disposable filtration device further includes a second filtration media interposed between the operative connection between the reusable base and the disposable filtration device for filtering air which enters the receptacle.

Another embodiment of the present invention is directed to a vacuum filtration apparatus that includes a disposable filtration device which includes a disposable filtration funnel capable of holding un-filtered liquid, a receptacle disposed below said funnel, said receptacle including a single opening located at the top of said receptacle, with the receptacle releasably attached to the funnel, and a filter disposed between the un-filtered liquid and the top of the disposable receptacle, with said filtered sealed to said filtration device to prevent the flow of unfiltered liquid into said receptacle. The apparatus also includes a reusable base releasably supporting said vacuum filtration device, and having an opening through which vacuum may be applied to said base, wherein the reusable base is operatively connected to the interior of said filtration receptacle so that the vacuum of said base may be applied to said filtration receptacle to draw liquid from said funnel, through said filter, into said filtration receptacle, and wherein said disposable filtration device further includes a second filtration media interposed between the operative connection between the reusable base and the disposable filtration device for filtering air which enters the receptacle.

Another embodiment of the present invention is directed to a vacuum filtration apparatus that includes a disposable filtration device that includes a disposable filtration funnel capable of holding unfiltered liquid, a disposable receptacle disposed below said funnel, said receptacle including a single opening located at the top of said receptacle, and a filter including an upstream side and a downstream side, disposed between the unfiltered liquid and the top of the disposable receptacle, with said filtered sealed to said filtration device to prevent the flow of unfiltered liquid into said receptacle. The apparatus also includes a reusable base releasably supporting said vacuum filtration device, and having an opening through which vacuum may be applied to said base, with the reusable base being operatively connected to the interior of said filtration receptacle so that the vacuum of said base may be applied to said filtration receptacle to draw liquid from said funnel, through said filter, into said filtration receptacle, and wherein the downstream side of the filter is in direct fluid flow communication with the interior of the receptacle.

Another embodiment of the present invention is directed to a vacuum filtration apparatus that includes a disposable filtration device that includes a disposable filtration funnel capable of holding un-filtered liquid, a disposable receptacle disposed below said funnel, said receptacle including a single opening located at the top of said receptacle, and a filter including an upstream side and a downstream side, disposed between the un-filtered liquid and the top of the disposable receptacle, with said filtered sealed to said filtration device to prevent the flow of un-filtered liquid into said receptacle. The apparatus also includes a reusable base releasably supporting said vacuum filtration device, and having an opening through which vacuum may be applied to said base, with the reusable base being operatively connected to the interior of said filtration receptacle so that the vacuum of said base may be applied to said filtration receptacle to draw liquid from said funnel, through said filter, into said filtration receptacle, and wherein the fluid flow path between the downstream side of the filter and the interior of the receptacle does not include a means to shut off the flow of liquid when the vacuum of the base is applied to the receptacle.

Another embodiment of the present invention is directed to a vacuum filtration apparatus that includes a disposable filtration device which includes a disposable filtration funnel capable of holding un-filtered liquid, a single disposable receptacle disposed below said funnel, said receptacle including a single opening located at the top of said receptacle, and a filter disposed between the un-filtered liquid and the top of the disposable receptacle, with said filtered sealed to said filtration device to prevent the flow of un-filtered liquid into said receptacle. The apparatus also includes a reusable base releasably supporting said vacuum filtration device, and having an opening through which vacuum may be applied to said base, wherein the reusable base is operatively connected to the interior of said filtration receptacle so that the vacuum of said base may be applied to said filtration receptacle to draw liquid from said funnel, through said filter, into said filtration receptacle.

Another embodiment of the present invention is directed to vacuum filtration apparatus that includes a disposable filtration device which includes a disposable filtration funnel capable of holding un-filtered liquid, a single receptacle disposed below said funnel, said receptacle including a single opening located at the top of said receptacle, with the receptacle releasably attached to the funnel, and a filter disposed between the un-filtered liquid and the top of the disposable receptacle, with said filtered sealed to said filtration device to prevent the flow of un-filtered liquid into said receptacle. The apparatus also includes a reusable base releasably supporting said vacuum filtration device, and having an opening through which vacuum may be applied to said base, with the reusable base being operatively connected to the interior of said filtration receptacle so that the vacuum of said base may be applied to said filtration receptacle to draw liquid from said funnel, through said filter, into said filtration receptacle.

Another embodiment of present invention is directed to a vacuum filtration apparatus that includes a disposable filtration device which includes a disposable filtration funnel capable of holding un-filtered liquid therein, a single receptacle disposed below said funnel, said receptacle including a single opening located at the top of said receptacle, a filter disposed between the unfiltered liquid and the top of the disposable receptacle, with said filtered sealed to said filtration device to prevent the flow of un-filtered liquid into said receptacle, and an inlet that is not a part of the receptacle, in fluid flow communication with said opening of said receptacle. The apparatus also includes a reusable base releasably supporting said vacuum filtration device, and having an opening through which vacuum may be Applied to said base, with the vacuum of said base being automatically applied to said inlet of said disposable filtration device when the disposable filtration device is placed onto the reusable base, thereby drawing liquid from said funnel, through said filter, into said filtration receptacle.

Another embodiment of the present invention is directed to a method of filtering a liquid comprising: 1) providing a vacuum filtration apparatus comprising: (a) a disposable filtration device comprising: a disposable filtration funnel capable of holding un-filtered liquid, a disposable receptacle disposed below said funnel, said receptacle including a single opening located at the top of said receptacle, a filter disposed between the un-filtered liquid and the top of the disposable receptacle, with said filtered sealed to said filtration device to prevent the flow of un-filtered liquid into said receptacle, with said disposable filtration device including an inlet, in fluid flow communication with the interior of said receptacle, and (b) a reusable base having an opening through which vacuum may be applied to said base, with said reusable base further including an outlet. The method also includes 2) placing the disposable filtration device onto the reusable base, thereby placing the outlet of said reusable base in fluid flow communication with the inlet of said disposable filtration device, thereby operatively connected to the interior of said filtration receptacle to the outlet of said base, 3) adding the liquid to be filtered to said funnel, and 4) applying vacuum to the outlet of said base, thereby drawing the liquid from said funnel, through said filter, into said filtration receptacle.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Illustrative embodiments related to vacuum filtration systems and portions thereof, as well as methods for filtration.

One embodiment of the present invention relates to a system that includes a filtering apparatus having receiving receptacle that is coupled to an adapter. The receiving receptacle receives a liquid to be filtered and may include a filtration element. The adapter is coupled between the receiving receptacle and an output receptacle that collects a filtered liquid. In addition, the system may include a base for supporting and directing a vacuum to the filtering apparatus.

Of course, the present invention is not limited to the entire system and may include portions thereof, as well as methods for use. In one embodiment, the system may be utilized to filter a cell culture medium.

Figure 1:
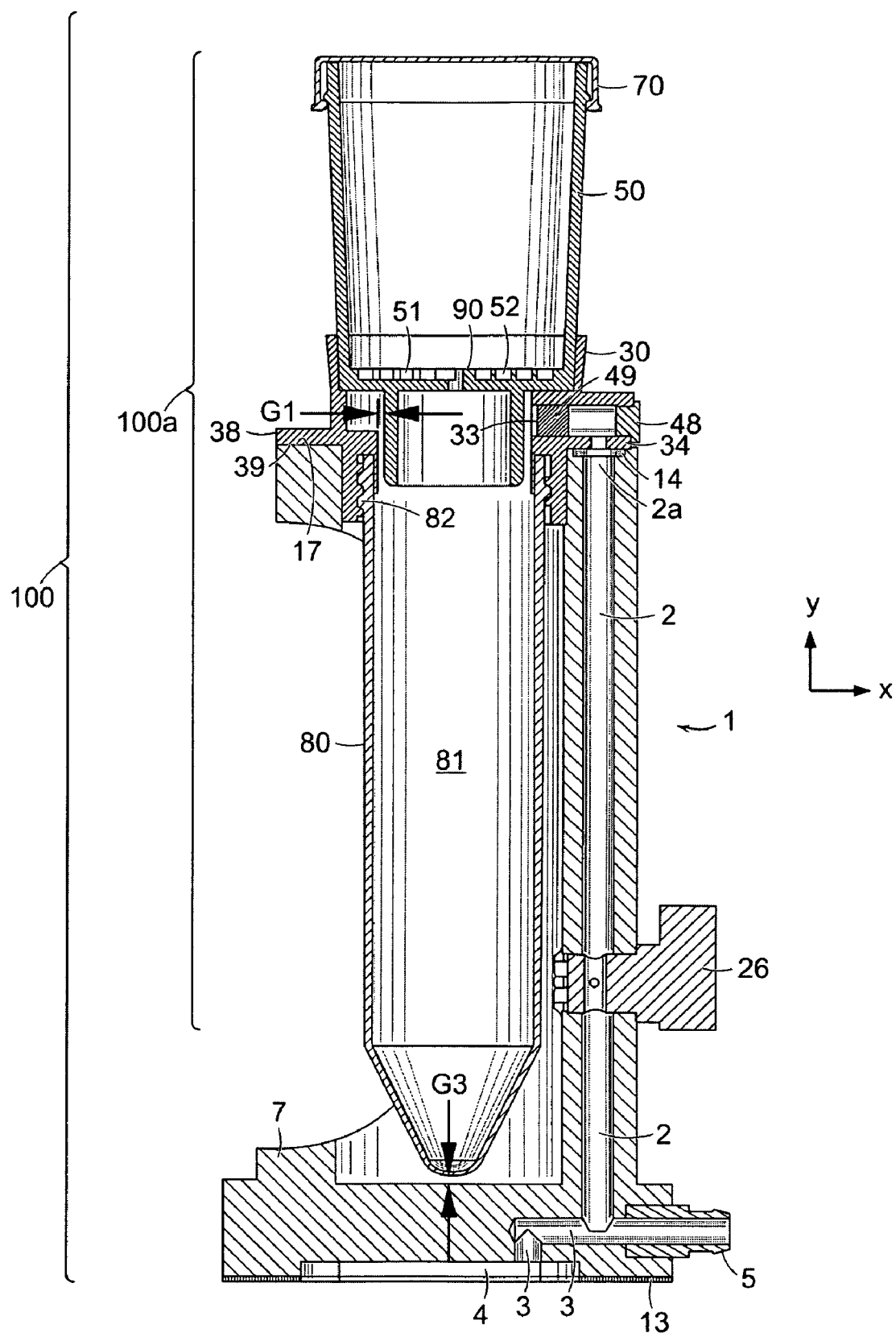
FIG. 1 is a cross-sectional view of one embodiment of a filtration system according to present invention in an operational assembly.

One embodiment of a filtration system 100 is shown in FIG. 1. The system 100 includes filtration apparatus 100a and a base 1 which both supports and directs a vacuum to the filtration apparatus 100a. The filtration apparatus 100a may include an adapter 30 and receiving receptacle 50. The receiving receptacle 50 may receive an unfiltered liquid to be filtered, and may include a filter element 90. The filtration apparatus 100a may also include an output receptacle 80 (shown as a disposable centrifuge tube) and optionally a lid 70. Of course, the output receptacle 80 may not be included in the system and the user may provide such a receptacle. The output receptacle 80 may be a glass bottle, a test tube or any other satisfactory device for receiving a liquid.

The output receptacle 80 may be releasably attached to adapter 30 via threads 82 of receptacle 80. For instance, the threads 82 may engage engaging threads 36 (FIG. 13) of an adapter 30. Seal 35 of the adapter 30 seals the interior 81 of output receptacle 80 to adapter 30 in a leak tight relationship. The output receptacle 80 may be releasably attached to the adapter using other means, such as a press fit between the output receptacle 80 and the adapter 30. Likewise, other means could be used to seal the output receptacle 80 to the adapter 30, such as a gasket placed between the top surface of the output receptacle 80 and the corresponding surface of the adapter 30.

Figure 2:
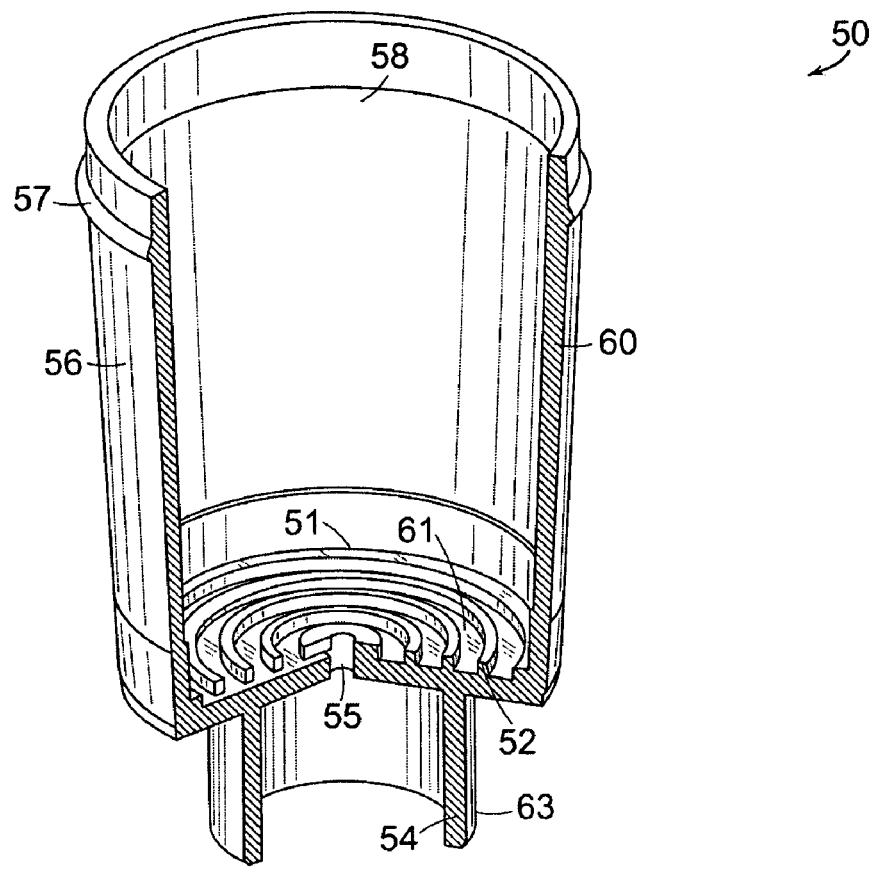
FIG. 2 is an isometric view, having portions thereof removed, of the receiving receptacle of the system depicted in FIG. 1.

FIG. 2 shows one embodiment of the receiving receptacle 50, which may include a filter element 90 (FIG. 1) that serves to prevent un-filtered liquid from entering the outlet 55 of receiving receptacle 50. The filter element 90 may be a microporous filter element, or a depth filter element, and may be either hydrophilic or hydrophobic depending upon the liquid to be filtered. Representative filter element materials include, cellulose nitrate, cellulose acetate, mix esters of cellulose, Teflon, PVDF, Nylon, polypropylene, polyethylene, polycarbonate, and glass fibers, but are not limited to these materials.

The receiving receptacle 50 receives a liquid to be filtered and may include side wall 60, filter seal surface 51, baffle 54, outlet 55, and a filter support. In this embodiment, the filter support includes filter support ribs 52 and channels 61. The filter support provides the proper support for filter element 90 and channels filtered liquid from the downstream side of filter element 90 into outlet 55. Other types of filter supports that provide the proper support for filter element 90 and that channels filtered liquid from the downstream side of filter element 90 into outlet 55 could be used to replace the filter support shown in FIG. 2.

The outer periphery of the downstream side of the filter element 90 may be sealed to filter seal surface 51, thereby preventing the flow of un-filtered liquid into the outlet 55.

Representative seals include a heat seal, an ultrasonic seal, a solvent seal, a glue seal, an RF seal, or a seal ring seal, or any other type of seal between any portion of the filter element and the funnel that prevents the flow of un-filtered liquid into outlet 55. Side wall 60 includes inner surface 58, outer surface 56, and may include lid clamp ring 57.

Receiving receptacle 50 may be non-releasably attached to the adapter 30 using an ultrasonic bond, a heat bond, a glue bond, a solvent bond, or any other type of leak tight bond, in which case the funnel and adapter are preferably made from the same materials, or of materials that can be easily bonded together. Materials may include acrylic, polycarbonate, styrene, polyethylene, and polypropylene. In applications where it is desired to releasably attach the receiving receptacle to the adapter, any of the releasable attachments disclosed in U.S. Pat. No. 6,913,152 could be used. Other types of releasable attachments could also be used.

Figure 3:
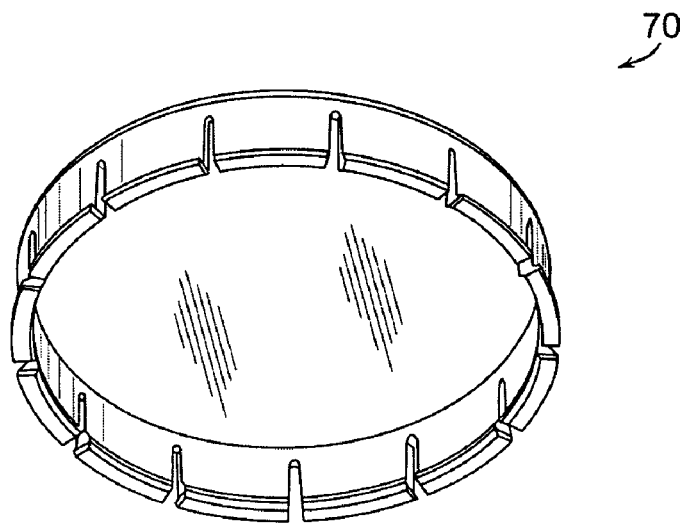
FIG. 3 is an isometric view of the lid component of the system depicted in FIG. 1.

FIG. 3 shows an illustrative embodiment of the lid 70, which may be type of lid releasably attached to receiving receptacle 50 by any of the methods disclosed in U.S. Pat. No. 6,913,152. Alternately other types of lids known in the art could also be used.

Figure 4:
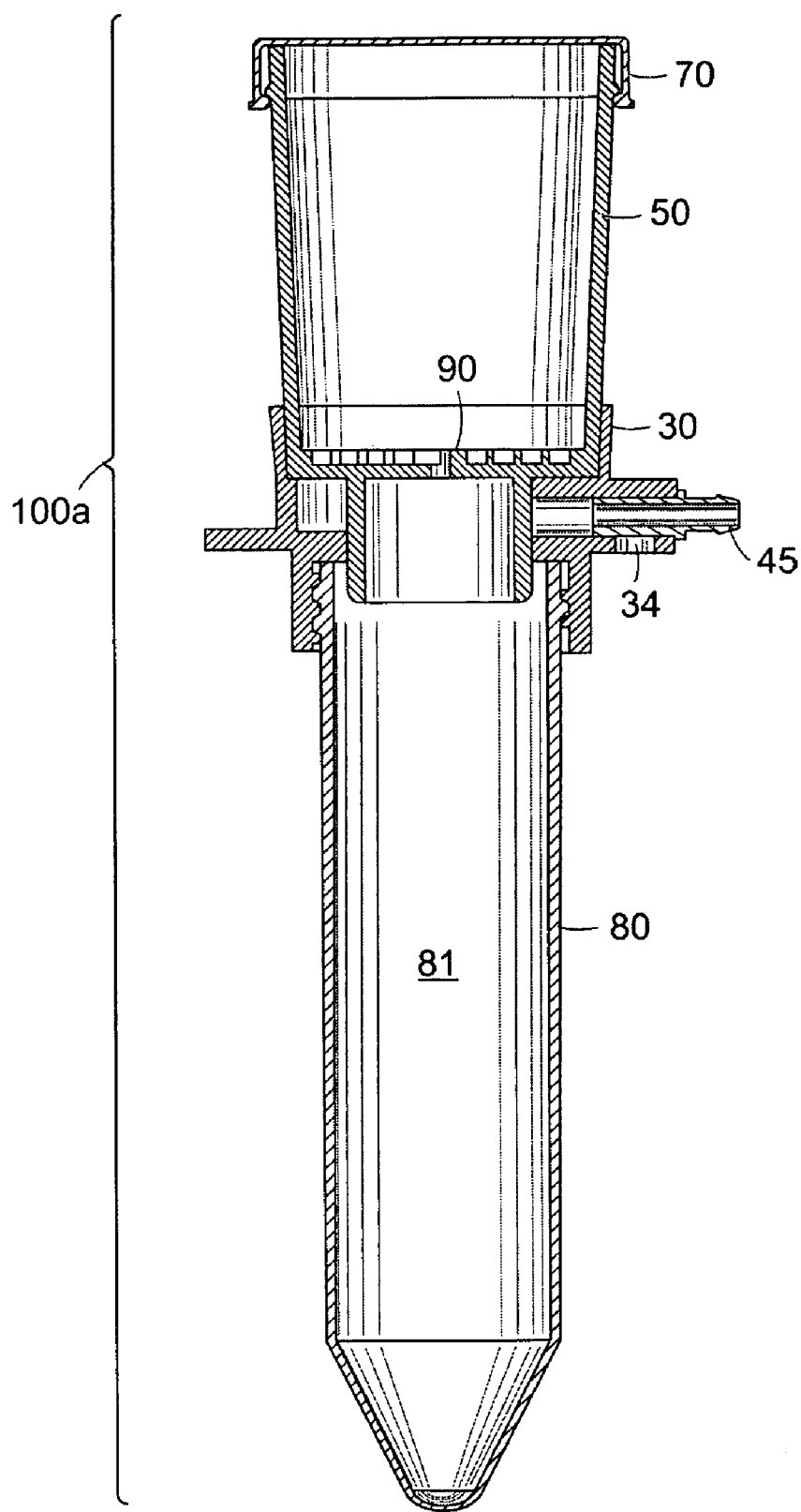
FIG. 4 is cross-sectional view of the filtration device depicted in FIG. 1, with a hose barb replacing the plug in the side inlet.

The filtration apparatus 100a may also include a plug 48 as shown in FIG. 1, when the filtration device is to be used with base 1. The plug 48 seals port 33a of the adapter 30. Alternately plug 48 may be replaced with a hose barb 45 (FIG. 4) thereby allowing disposable filtration device 100a to be used without the base 1. Alternatively, the plug 48 could be integral part of adapter 30.

Referring again to FIG. 1, one embodiment of a base 1 is shown. As noted above, the base 1 of this and other embodiments serves to support the filtration apparatus. In some embodiments the base supports the filtration apparatus in such a manner that the output receptacle 80 is suspended above the bottom portion 7 such that a gap G3 exists therebetween.

This embodiment includes an internal vacuum channel comprised of at least conduit 2 and may also include conduit 3 and terminates at a delivery port 2a. The delivery port 2a, when in operation, mates with the adapter 30 to create a seal so that a vacuum may be created in the output receptacle 80.

As shown in FIG. 1, this embodiment of the base 1 includes a bottom portion 7 and may also include hose barb 5, gasket 13, three-way valve 26, and seal 14. The seal 14 is shown as an o-ring, but could be any type of seal such as a gasket or the like.

Figure 5:
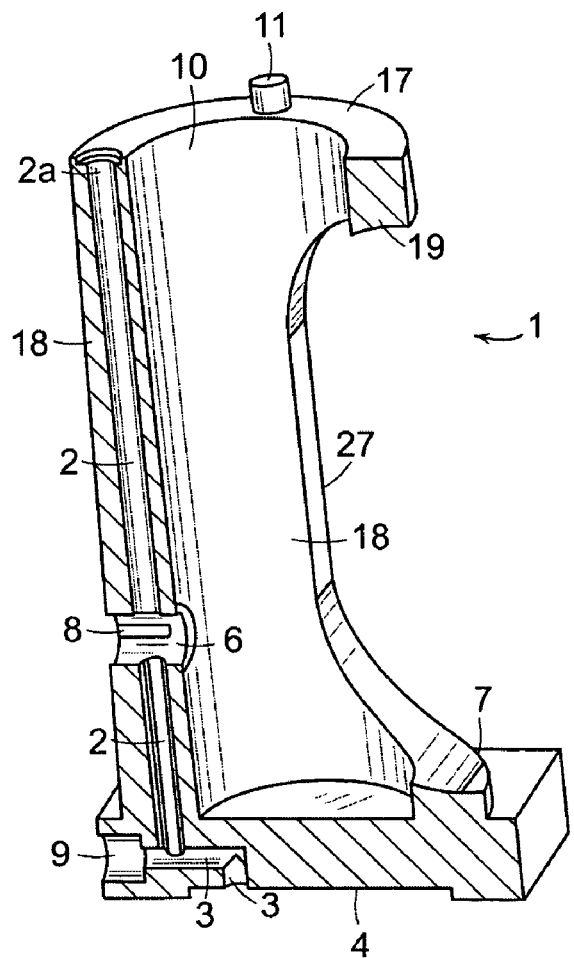
FIG. 5 is an isometric view, having portions thereof removed, of the base depicted in FIG. 1.

As shown in FIG. 5, which is cut-away view of the base 1 shown in FIG. 1, the base 1 may include base support member 7, side wall 18, and device support member 19. Side wall 18 supports device support member 19 so that support surface 17 of device support member 19 is located at the desired distance above the top of base support member 7. Side wall 18 preferably includes side wall relief 27 (i.e., the front and a portion of both sides of side wall 18 are cut away) to make the receiving receptacle visible during the filtration cycle.

The device support member 19 preferably includes at least one registration detail, such as an align pin 11, that is used to properly align the filtration device 100a on the base 1. The device support member 19 in conjunction with one align pin 11, properly aligns the filtration device 100a on the base 1.

Figure 13:
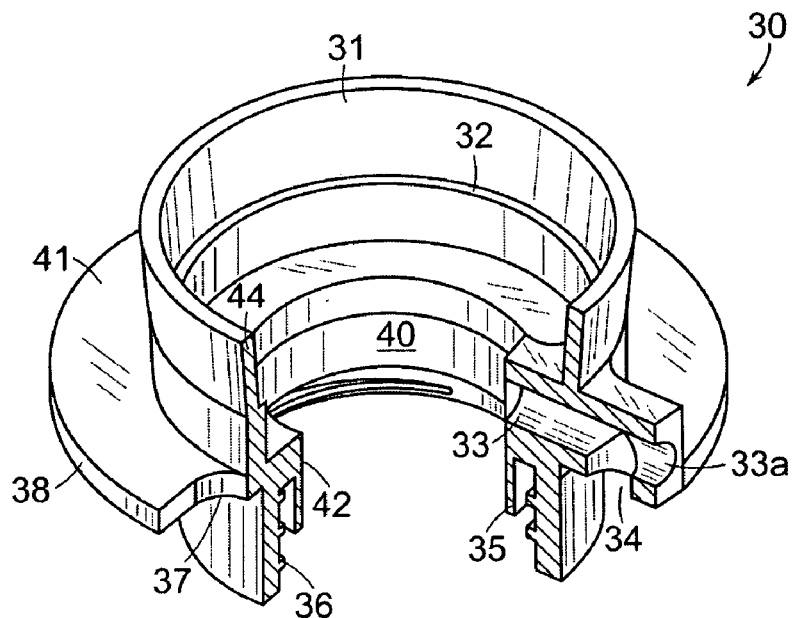
FIG. 13 is an isometric view, having portions thereof removed, of the adapter component of the filtration device depicted in FIG. 1.

The base 1 also includes a vacuum inlet 9, which is in fluid flow communication with conduit 2 and conduit 3. Conduit 3 places vacuum inlet 9 in fluid flow communication with base vacuum chamber 4, but may be omitted. Conduit 2 includes a delivery port 2a that places the vacuum inlet 9 in fluid flow communication with bottom inlet 34 of adapter 30 (FIG. 13).

The base 1 may be made of a substantially rigid material and the conduits 2 and 3 comprise an internal vacuum chamber therein. In some embodiments the internal vacuum chamber is entirely within the base 1. The delivery port 2a may be referred to herein as a "base vacuum delivery port".

Figure 6:
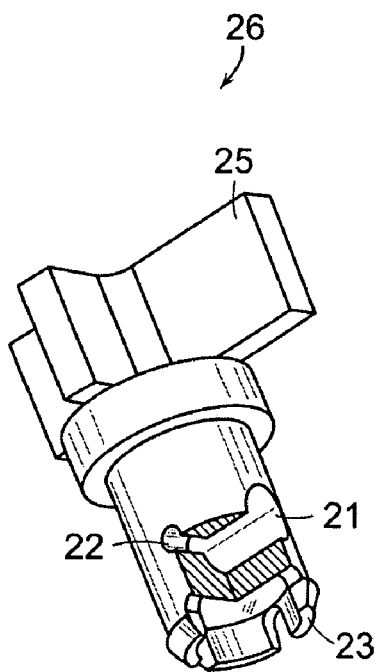
FIG. 6 is an isometric view, having portions thereof removed, of the three-way valve depicted in FIG. 1.
Figure 7:
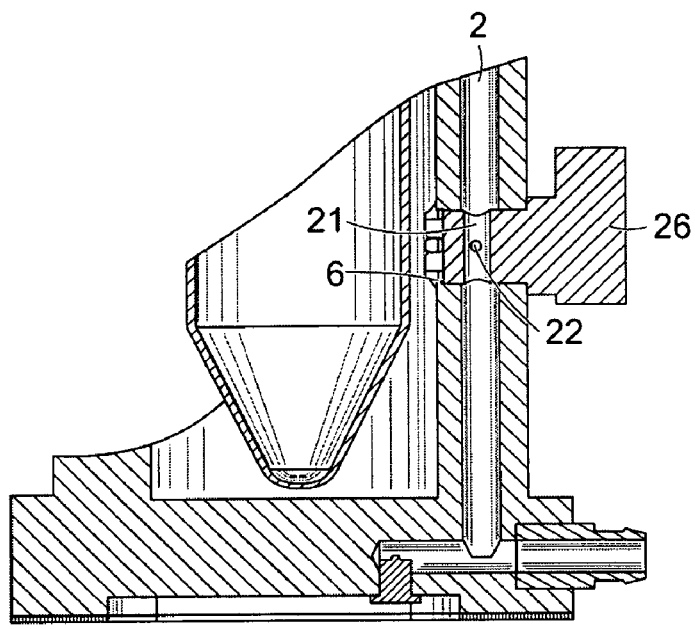
FIG. 7 is a partial cross-sectional view of a bottom portion of the base depicted in FIG. 1, with the three-way valve in the open position, and with a plug in the conduit that leads to the base vacuum chamber.
Figure 8:
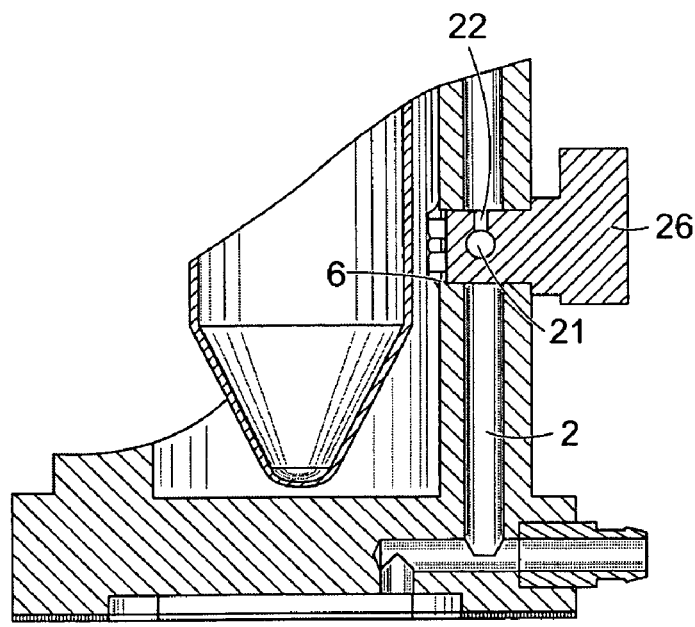
FIG. 8 is a partial cross-sectional view of a bottom portion of the base depicted in FIG. 1, with the three-way valve in the closed position, and without a plug in the conduit that leads to the base vacuum chamber.

In FIGS. 5 and 6, the base 1 may also include a valve hole 6, which in turn forms a vent slot 8 containing a three-way valve may be used. As shown in FIG. 6, three-way valve 26 includes vacuum port 21, vent port 22, snap fit tabs 23, and handle 25. Three-way valve 26 snaps into valve hole 6 of base 1 as shown in FIG. 1. In alternative embodiments, the three-way valve 26 may be attached to base 1 by other than the snap fit tabs disclosed herein. As an example, FIG. 7 shows the three-way valve 26 in the open position with vacuum port 21 connecting the top and bottom portions of conduit 2, and with vent port 22 blocked off by the side wall of valve hole 6 that does not include vent slot 8. FIG. 8 shows the three-way valve 26 in the closed position with vent port 22 and vacuum port 21 in fluid communication with vent slot 8.

Among other things, the base 1 may be cast or machined from materials, such as urethane, or epoxy, or could be either cast or machined from materials, such as stainless steel or aluminum, or molded or machined from plastics such as polycarbonate, acrylic, or polysulfone.

Figure 9:
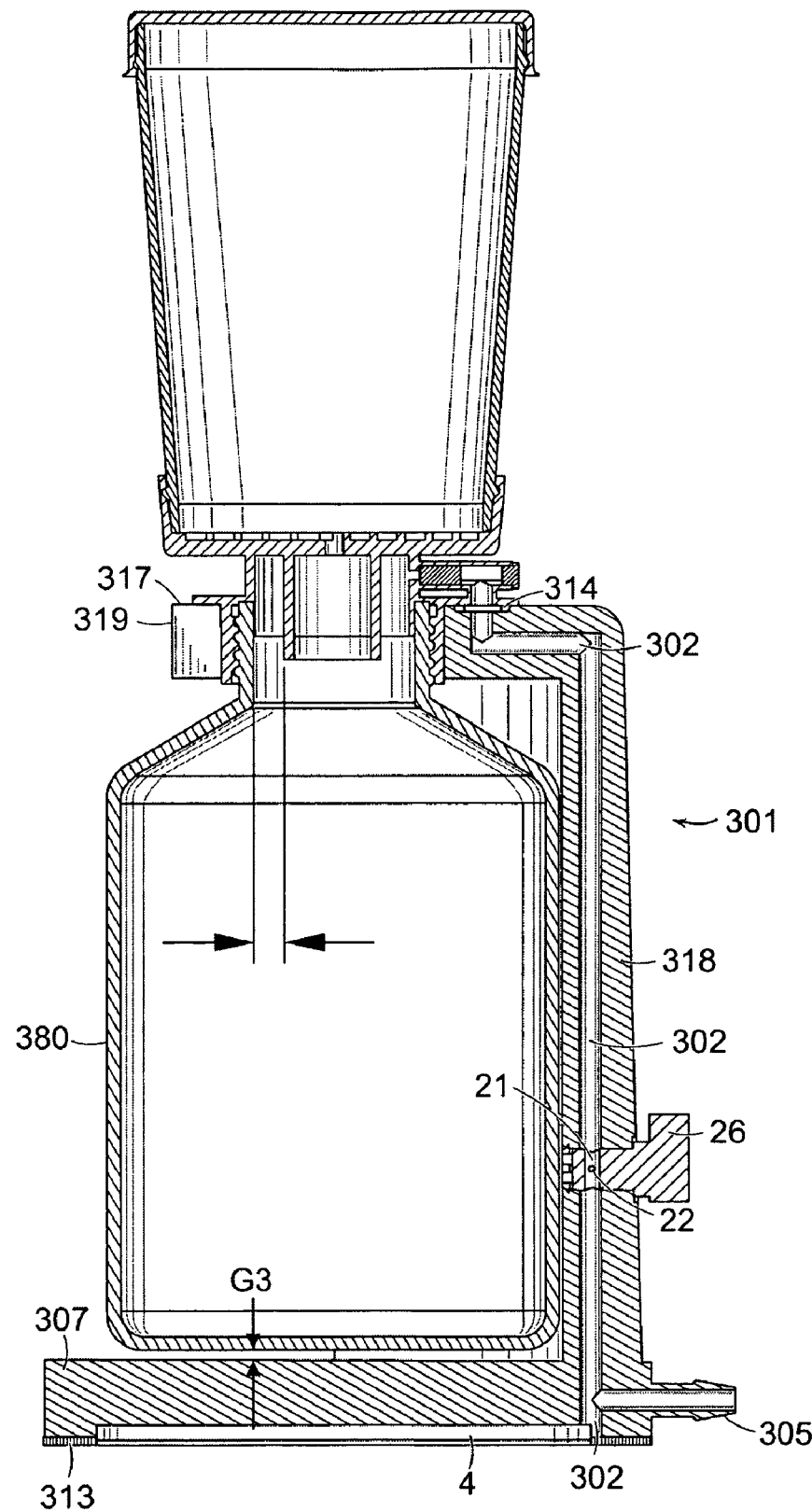
FIG. 9 is a cross-sectional view, of another embodiment of a base according the present invention.

Another embodiment of a base 301 and a receiving receptacle 380 (i.e., a bottle) is shown in FIG. 9. The base 301 of this embodiment includes a lower portion 307, a gasket 313, three-way valve 26, and seal 314 shown as an o-ring, but could be any type of seal, such as a gasket. The base 301 includes a side wall 318 having vacuum channel 302 disposal therein and device support member 319, and integral hose barb 305. Side wall 318 supports device support member 319 so that support surface 317 of device support member 319 is located at the desired distance above the lower portion 307. The device support member 319 may include one or more registration details, such as align pins, to properly align the disposable filtration device on the base.

Figure 10:
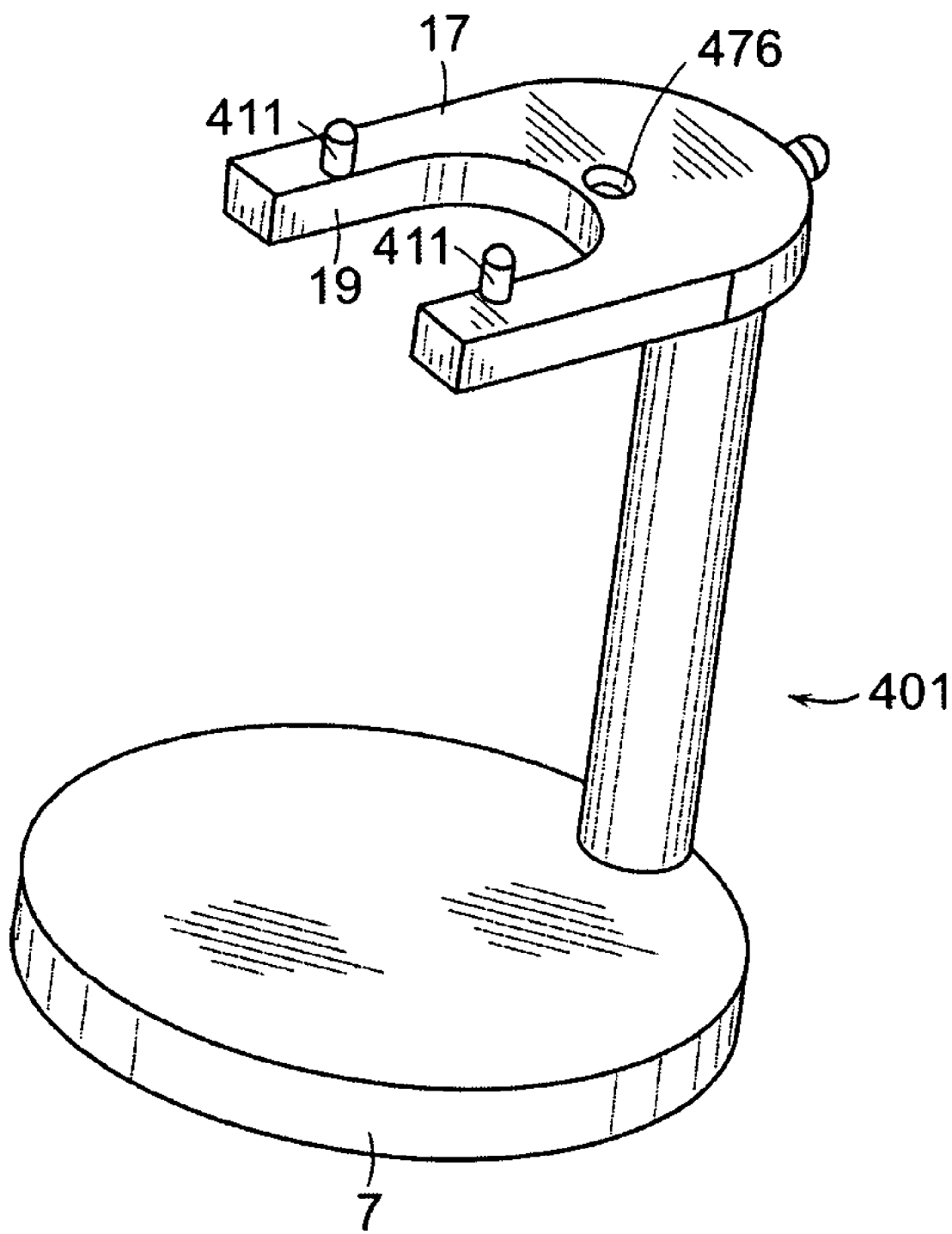
FIG. 10 is an isometric view, of another embodiment of a base according to the present invention.

Another embodiment of a base is shown in FIG. 10. The base 401 portions are similar to the previous embodiments. In addition, base 401 may include one or more align pins 411, that are used to properly align the filtration device on the base.

Figure 11:
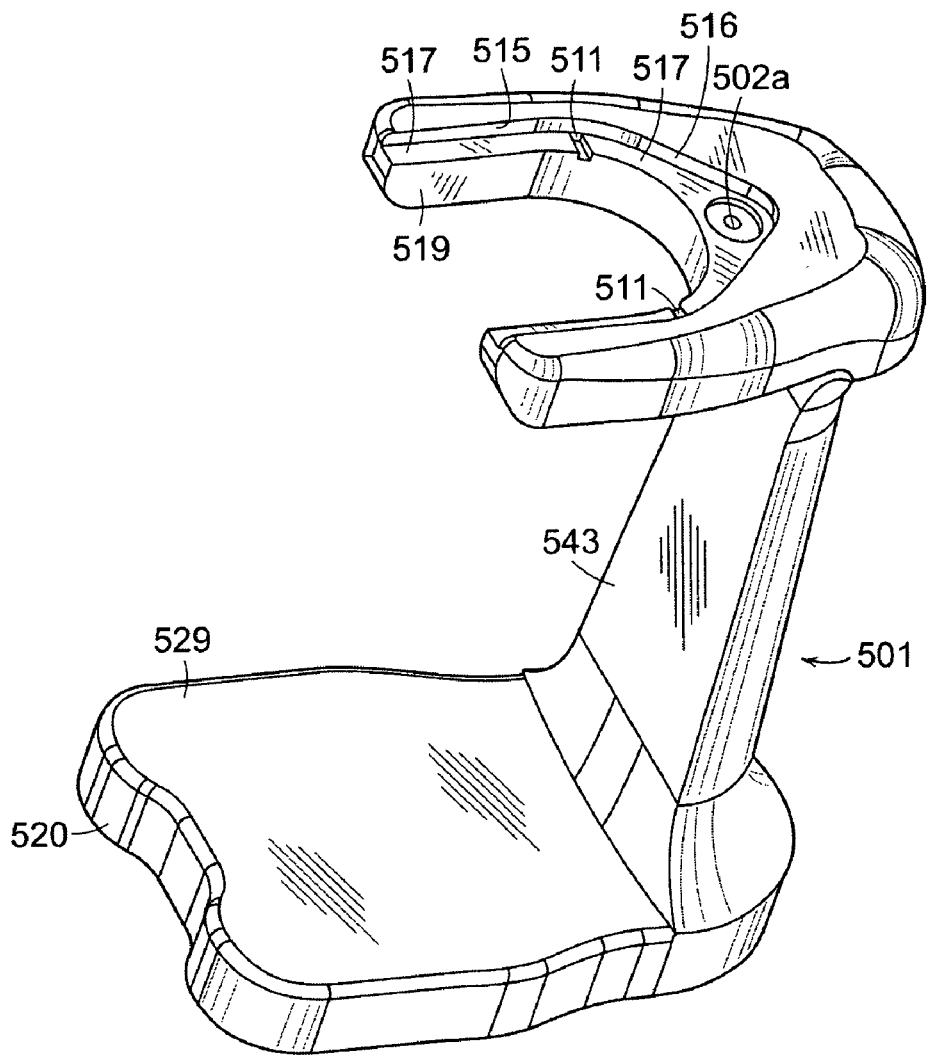
FIG. 11 is an isometric view, of a base according to the present invention.
Figure 12:
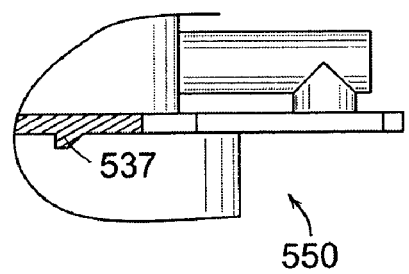
FIG. 12 is a partial cross-sectional view of an align pin of a receiving receptacle adapted to mate with the a base.

Another embodiment of a base is shown in FIG. 11. The base 501 of this embodiment includes base support member 520, side wall 543, and device support member 519. The side wall 543 supports device support member 519 so that support surface 517 of device support member 519 is located at the desired distance above the top 529 of base support member 520. The device support member 519 may include at least registration details 511 (two registration details are shown in FIG. 11) that are used to align and lock in place the disposable filtration device on the base 501. For instance, the registration detail 511 could mate with a corresponding registration detail 537 of the adapter 550 shown in FIG. 12.

In addition to the registration details, the base 501 may also include a well 516 defined by support surface 517 and side wall 515. The shape of side wall 515 may be designed so that it matches the shape of the flange on an adapter of any of the adapter embodiments described herein. In addition, this embodiment includes an internal vacuum chamber (not shown) that terminates at the base vacuum delivery port 502a.

Figure 14:
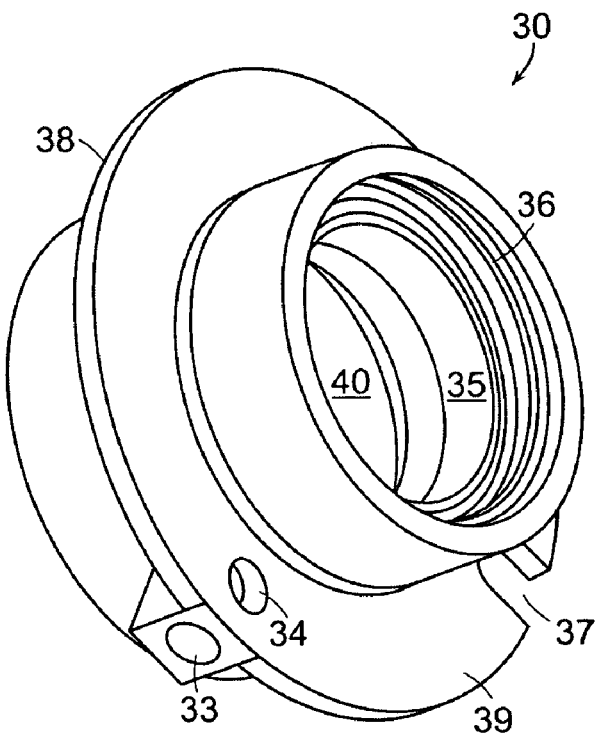
FIG. 14 is a bottom isometric view of the adapter of the filtration device depicted in FIG. 1.

FIGS. 13 and 14 show one example of an adapter 30 according to the present invention. The adapter 30 of this embodiment may include a flange 38, side inlet 33, bottom inlet 34, seal 35, and threads 36. Flange 38 includes top surface 41, bottom surface 39, and at least one align slot 37. The adapter 30 may also include either plug 48 (FIG. 1) or hose barb 45 (FIG. 4), and may also include a filter element located inside inlet 33. In the event the side inlet 33 is filled with a hose barb, the filtering system may be used without a base 1 as the bottom inlet 34 is filled by the hose barb.

The flange 38 may define the outer periphery of the adapter 30. The bottom surface 39 of the flange 38 includes a bottom inlet 34. When in use, the bottom inlet 34 is aligned with the base vacuum delivery port 2*a* of any of the embodiments of the base disclosed herein. The alignment of the bottom inlet 34 with a base vacuum delivery port serves to create a vacuum in the output receptacle 80 when a vacuum is applied to the internal vacuum channel of the base.

The seal 35 seals the interior of an output receptacle attached to the adapter 30 in a leak tight relationship. In some embodiments, the adapter may include threads 36 to mate with corresponding threads on an output receptacle.

The adapter 30 may also include a center hole 40 through which fluid will pass when in operation. The adapter 30 may also include side wall 44 that has inner surface 31 and step 32. The step 32 may support a receiving receptacle 50 when coupled to the adapter 30.

The flange 38 may also include a registration detail 37. The registration detail 37 is shown as a slot but could be any detail capable of ensuring that the bottom inlet 34 is aligned over the base vacuum outlet port 2*a* when the adapter 30 is coupled to a base. In one embodiment, the registration detail may require that the adapter 30 only be coupled to the base in one particular orientation (i.e., alignment of the two noted parts) and may, in some embodiments, guide the adapter to that particular orientation. In some embodiments, the base may have a corresponding registration detail to mate with the registration detail 37 of the adapter 30. Of course, the adapter 30 could have more than one registration detail. Examples of other types of registration details that could be included in the adapter 30 include, but are not limited to, a protrusion, a recess, a pin, a slot, and the like. In some embodiments the registration details may serve to automatically connect the bottom inlet 34 with the base vacuum outlet port 2*a*. In some embodiments this may advantageously allow a user to place the filtration device 100*a* on the base 1 with 1 hand.

Figure 15:
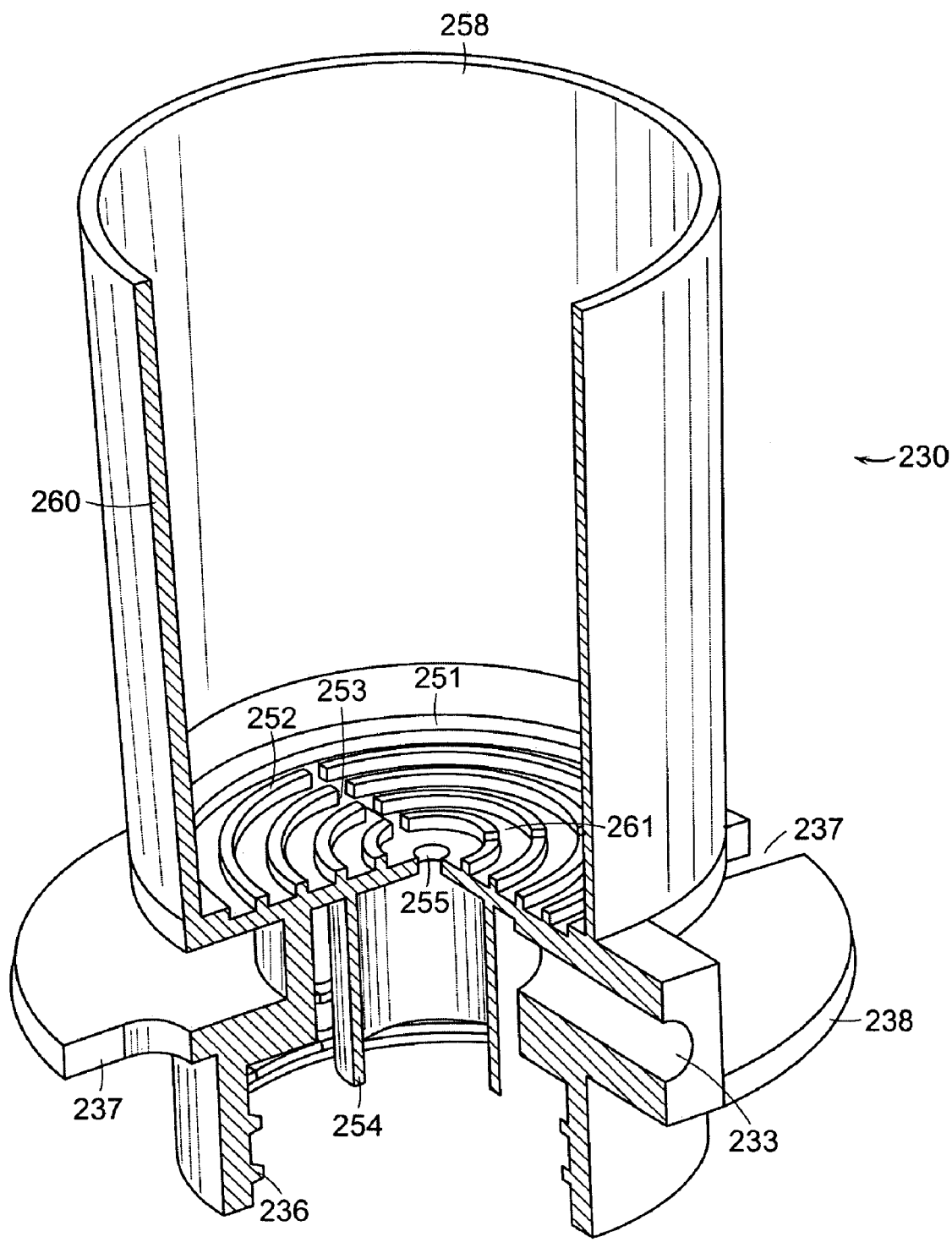
FIG. 15 is an isometric view, having portions thereof removed, of the adapter component including an integral receive receptacle.

Of course, the adapter 30 could be modified depending on the application. For example, and as shown in FIG. 15, the adapter 230 may include a flange 238, side inlet 233, threads 236, and an integral receiving receptacle 258. In this embodiment, the flange 238 may also include one or more registration details 237. The integral receiving receptacle 258 includes a side wall 260, filter seal surface 251, baffle 254, outlet 255, and a filter support. The filter support includes filter support ribs 252 and channels 261, and at least one radial channel 253. The filter support provides the proper support for a filter element 90 (not shown) and channels filtered liquid from the downstream side of filter element 90 into outlet 255. Any type of filter that provides the proper support for filter element 90, and channels filtered liquid from the downstream side of filter element 90 into outlet 255 could be used to replace the filter support means shown in FIG. 15. The outer periphery of the downstream side of filter element 90 may be sealed to filter seal surface 251, thereby preventing the flow of unfiltered liquid into the outlet 255.

Figure 16:
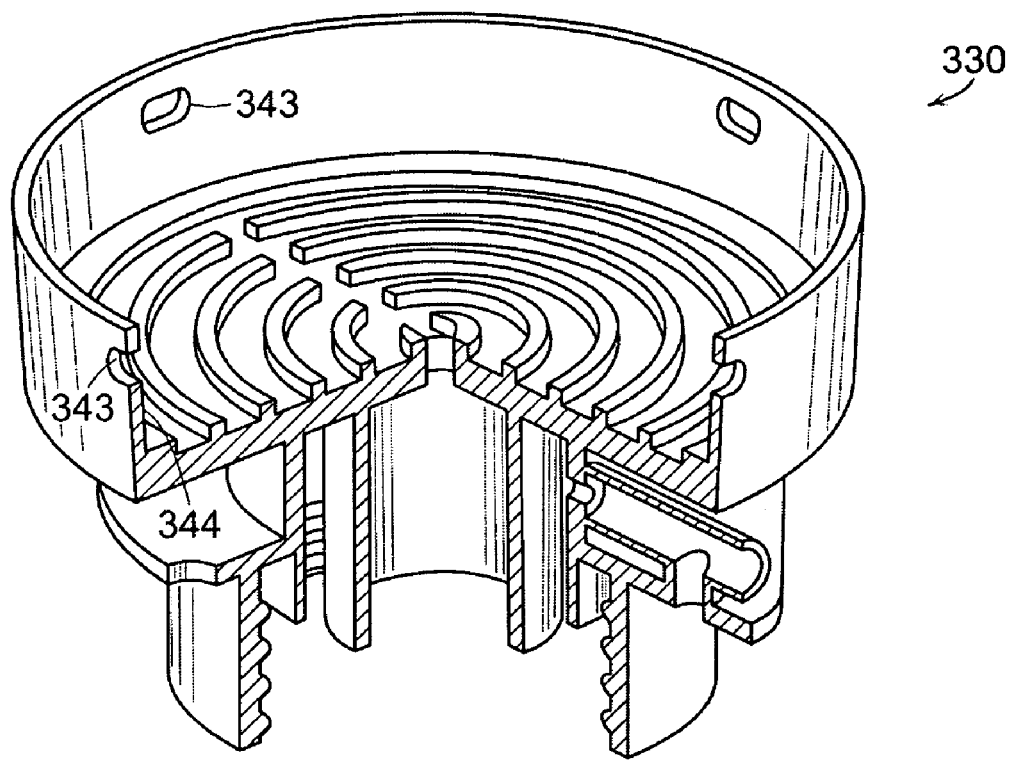
FIG. 16 is an isometric view, having portions thereof removed, of another embodiment of an adapter.
Figure 17:
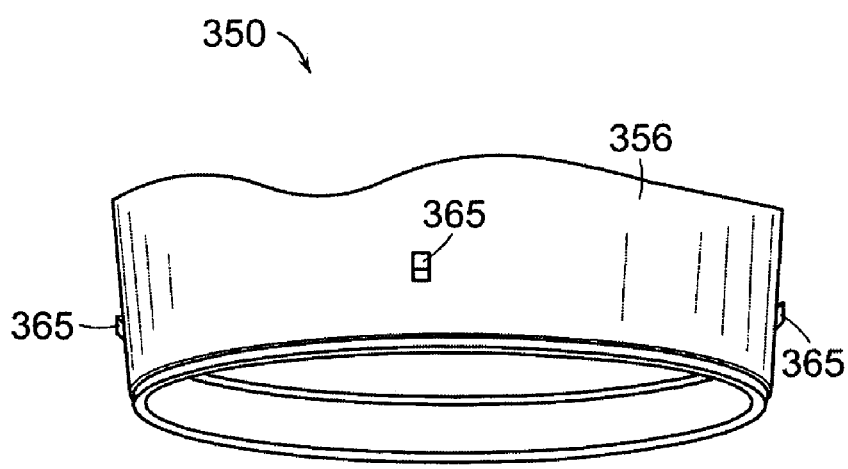
FIG. 17 is a partial isometric view of the bottom portion of the receive receptacle depicted in FIG. 16, showing the funnel locking pins.

Another embodiment of an adapter is shown in FIG. 16. The adapter 330 in this embodiment, unlike the previous embodiment, does not have an integral receiving receptacle but, rather, includes a side wall 344 having one or more slots 343. The receiving receptacle 350 shown in FIG. 17 may include complementary protrusion 365 in its sidewall 356 to lock the receiving receptacle into the adapter 330.

Figure 18:
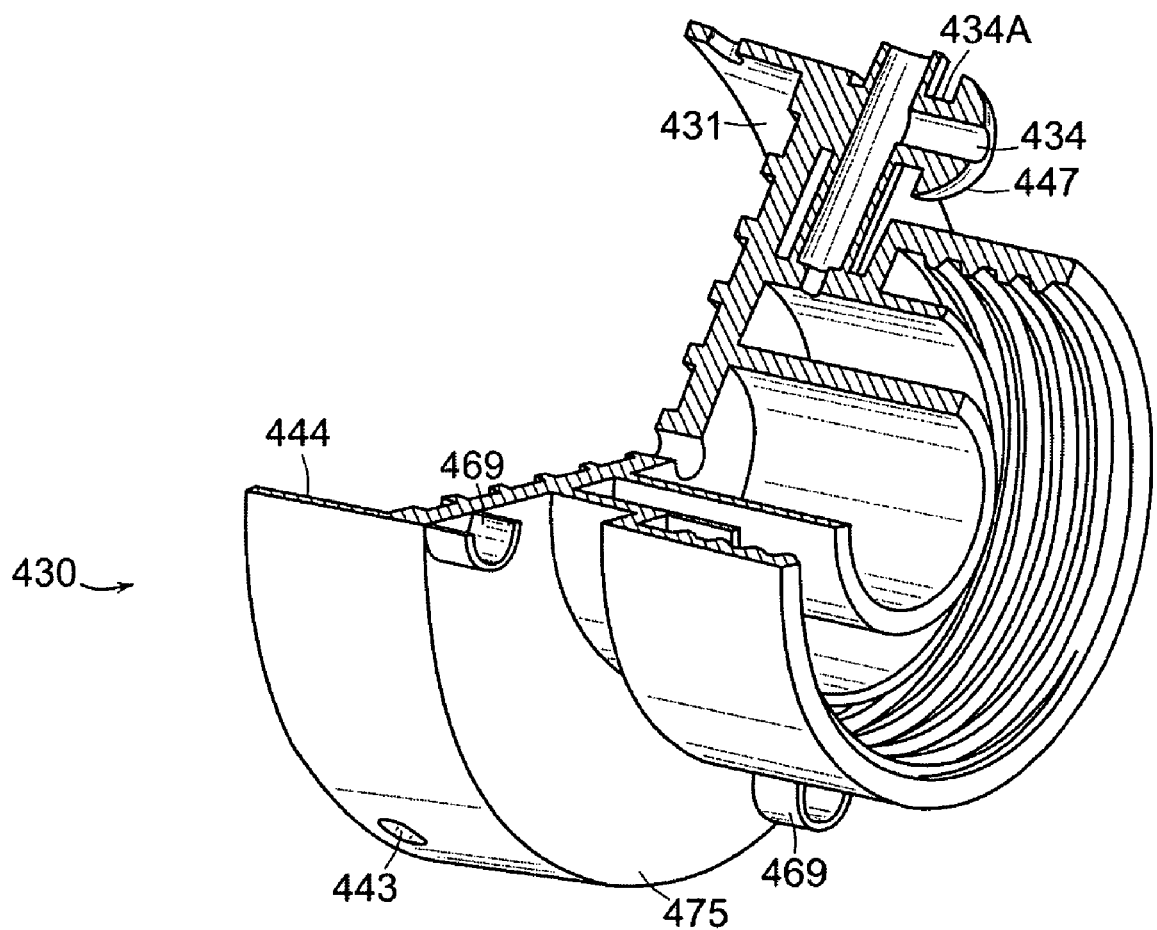
FIG. 18 is a bottom isometric view, having portions thereof removed, of another embodiment of an adapter.

In another embodiment, and as shown in FIG. 18, the adapter 430 does not include a flange 38. In this embodiment, the adapter 430 includes a side wall 444 having an inner surface 431 and at least one slot 443. One or more align rings 469 extend from a lower surface 475 of adapter 430. These align rings are designed to mate, for example, with the pins 411 on the base 401 shown in FIG. 10. The bottom of side wall 434*a* of bottom inlet 434 may include a spherical surface 447 which may mate with the base vacuum delivery port 476 of the base 401 shown in FIG. 10.

Various embodiments of the present invention and portions thereof have been described above. In general the systems described herein may operate as follows with reference to FIG. 1.

The end user may provide the filtration device 100*a* by either purchasing a complete assembly or an assembly without an output receptacle 80, in which case the user will attach an output receptacle (preferably pre-sterilized) to the adapter 30. The user then places the base 1 on a flat surface and connects a vacuum hose thereto, for example, via hose barb 5. The other end of the vacuum hose may be connected to a vacuum source.

If a three way valve 26 is present, it initially may be turned to the off position. The user may start a vacuum source to evacuate base vacuum chamber 4 of the lower portion 7 of the base 1 to hold the base 1 in place. Of course, vacuum chamber 4 could be omitted and this step skipped.

The user then may place the filtration device 100*a* with a output receptacle 80 (attached to adapter 30), onto reusable base 1, by inserting receptacle 80 into hole 10 (FIG. 5) of base 1 until bottom surface 39 of flange 38 of adapter 30 contacts support surface 17 of base 1. The user adjusts the orientation until there is a registration fit with align pin 11 (FIG. 5) of base 1 and align slot 37 (FIG. 13) of adapter 30. This alignment aligns the bottom inlet 34 of adapter 30 with base vacuum channel output port 2*a* of conduit 2. Of course, in this and other embodiments the align pin 11 and the align slot 37 could be eliminated and the user could manually align the filtration device 100*a* so that inlet 34 aligns with port 2*a*.

When filtration device 100*a* is properly positioned on base 1 as shown in FIG. 1, a gap G3 will exist between the bottom of receptacle 80 and the bottom portion 7 of the base 1. Of course the gap G3 could also be between the bottom of the receptacle 80 and the surface on which the base 1 sets. When spaced in this manner, the receptacle 80 (and filtering apparatus 100*a*) is considered to be suspended by the base.

As shown in FIG. 1, the support upper surface 17 of the support is arranged so that it is upstream of the output receptacle 80. As used herein, upstream means a location above another location in a direction opposite to that in which a fluid would flow if orientated as shown. Here, upstream means that the support is above the output receptacle in the "Y" direction.

During actual use, a user may remove the lid 70 from receiving receptacle 50, and pour a quantity of un-filtered liquid (such as cell culture media) into the interior of receiving receptacle 50, upstream of filter element 90. The lid 70 may then be reattached to receiving receptacle 50 as shown in FIG. 1. The user then simply turns three-way valve to the on position shown in FIG. 1, thereby evacuating the interior 81 of receptacle 80. If the inside surface area of the seal 14 is larger than the cross-sectional area of bottom inlet 34 of adapter 30 as shown in FIG. 1, the vacuum at base vacuum outlet port 2*a* of conduit 2 of base 1 will create a downward force on the surface area of bottom surface 39 of flange 38 of adapter 30 that is encircled by seal 14, thereby creating a downward force on said area and firmly holding disposable filtration apparatus 100*a* in place on base 1.

The initial air in the interior 81 of receptacle 80, and in the filter support means of receive receptacle 50, will flow from the interior of output receptacle 80; through gap G1 between inner surface 42 of adapter 30 and outer surface 63 of baffle 54 (FIG. 2); into side inlet 33 of adapter 30; through filter element 49 (if filter element 49 is used); through bottom inlet 34; into inlet 2a of conduit 2, through conduit 2; through vacuum inlet 9 of the base 1; and into the vacuum source.

The top surface of the un-filtered liquid in receiving receptacle 50 will be kept at atmospheric pressure via a venting means in either the receiving receptacle or the lid 70. Therefore the positive pressure of the liquid at the level of the upstream surface of filter element 90 will be proportional to the height of the liquid in the receiving receptacle. Therefore, a differential pressure will exist between the positive pressure of the liquid on the upstream side of the filter element and the negative pressure on the downstream side of the filter element, created by evacuating the interior of the output receptacle 80. As the interior 81 of output receptacle 80 is evacuated, un-filtered liquid from receiving receptacle 50 will pass through filter element 90. The filtered liquid on the downstream side of filter element 90 will then pass through outlet 55 of receiving receptacle 50, into output receptacle 80. This process will continue until all of the un-filtered liquid has been filtered and collected in output receptacle 80.

After all of the liquid has been filtered and collected in output receptacle 80, the user may turn three-way valve 26 to the closed position and, thus, vent to atmosphere the interior of output receptacle 80, the upper part of conduit 2, bottom inlet 34, side inlet 33, and the filter support of the receiving receptacle 50, by allowing external air to enter vent slot 8 of base 1 (FIG. 5); and then pass through vacuum port 21 and vent port 22 of three-way valve 26 (FIG. 6); through the upper portion of conduit 2 of base 2; through bottom inlet 34, and side inlet 33 of adapter 30; through filter element 49; into the interior of output receptacle 80.

In some embodiments, optional filter element 49 may prevent non-sterile air from entering the interior of output receptacle 80. The user may then remove disposable filtration device 100a from the base 1 and then remove the output receptacle from adapter 30, attach a closure to the top of output receptacle 80 (closure not shown), and discard the remaining components of disposable filtration device 100a in a safe manner. The receptacle along with its contents can now be either used or stored. If three-way valve 26 is not used, then the vacuum would be turned on, and turned off, and vented externally to the reusable base.

Although the present invention has been shown and described in terms of specific preferred embodiments, it will be appreciated by those skilled in the art that changes or modifications are possible which do not depart from the inventive concepts described and taught herein. Such changes and modifications are deemed to fall within the purview of these inventive concepts. Any combination of the various features of the preferred embodiments are deemed to fall within the purview of these inventive concepts.

What is claimed is:

1. A liquid filtering system comprising:
a filtering apparatus having a receiving receptacle coupled with an adapter having an adapter channel terminating at a generally planar surface defining an adapter port for receiving a vacuum, the adapter port being substantially unmovable relative to any part of the adapter channel, the adapter also having an interface for removably coupling with an output receptacle for receiving filtered liquid from the filtering apparatus, the adapter being configured to couple between the receiving receptacle and output receptacle; and a base suspending the receiving and output receptacles and having a substantially rigid housing containing an internal vacuum channel terminating at a base vacuum delivery port, the base vacuum channel terminating at a generally planar surface defining the base vacuum delivery port, the base vacuum delivery port being substantially unmovable relative to the base vacuum channel, the adapter being removably couplable with the base to connect the adapter port to the base vacuum delivery port and to suspend the receiving and output receptacles, the adapter configured so that the adaptor port generally planar surface abuts the base vacuum delivery port generally planar surface to fluidly connect the base vacuum delivery channel and the adapter channel.

2. The system as defined by claim 1 wherein the filtering apparatus also comprises a cell culture medium filter for filtering a liquid received by the receiving receptacle.

3. The system as defined by claim 1 further comprising the output receptacle coupled with the adapter interface.

4. The system as defined by claim 3 wherein the output receptacle comprises threads that mate with corresponding threads in the interface.

5. The system as defined by claim 1 further comprising the output receptacle coupled with the adapter interface, the base having a bottom portion, the base suspending the output receptacle above the bottom portion to form a gap therebetween.

6. The system as defined by claim 1 wherein the housing defines the vacuum channel.

7. The system as defined by claim 1 wherein at least one of the adapter port and the base vacuum delivery port comprises a gasket.

8. The system as defined by claim 1 wherein at least one of the filtering apparatus and base has two registration details that prevent the filtering apparatus from rotating relative to the base, the registration details being configured to provide a registration coupling in a manner that connects and substantially locks the base vacuum delivery port with the adapter port.

9. The system as defined by claim 8 wherein the filtering apparatus has a first aligning detail, the base having a second aligning detail, the first and second aligning details being in registry while the base is coupled with the adapter to align the base vacuum delivery port with the adapter port.

10. The system as defined by claim 1 wherein the base has a vacuum receiving port for receiving a vacuum from an external source, the internal vacuum channel being between the vacuum receiving port and the base vacuum delivery port.

11. The system as defined by claim 1 wherein the receiving receptacle comprises a funnel.

12. The system as defined by claim 1 wherein the receiving receptacle is an integral part of the adapter.

13. A liquid filtering system comprising:
a filtering apparatus having a receiving receptacle coupled with an adapter, the adapter including a vacuum channel terminating at a port defined by a generally planar surface;

an output receptacle for receiving filtered liquid from the filtering apparatus; and a substantially rigid base couplable with the adapter, the base having a coupling portion configured to suspend the filtering apparatus and output receptacle, the coupling portion having a base vacuum channel terminating at a base vacuum port defined by a generally planar surface, the coupling portion fluidly connecting the base vacuum channel of the coupling portion and the output receptacle by abutting the generally planar surfaces while suspending the output receptacle.

14. The system as defined by claim 13 wherein the base has a bottom portion, the output receptacle being spaced from the bottom portion.

15. The system as defined by claim 13 wherein the vacuum channel is contained substantially entirely within the base, the vacuum channel connecting with the adapter to provide a vacuum.

16. The system as defined by claim 13 wherein the output receptacle is removably couplable with the filtering apparatus.

17. The system as defined by claim 13 wherein the base is removably couplable with the adapter.

18. The system as defined by claim 13 wherein the filtering apparatus and base are configured to provide a registration coupling in a manner that connects the vacuum channel with the adapter.

19. The system as defined by claim 13 wherein the receiving receptacle is an integral part of the adapter.

20. A liquid filtering system comprising:
a filtering apparatus having a receiving receptacle coupled with an adapter, the adapter having an adapter vacuum channel terminating at an adapter port positioned at a substantially fixed location relative to the adapter vacuum channel, the adapter port being defined by an exterior, generally planar surface of the adapter vacuum channel;
an output receptacle for receiving filtered liquid from the filtering apparatus; and
a substantially rigid base having a rigid coupling portion with a base vacuum channel, the coupling portion being configured for removably supporting and suspending the receiving and output receptacles and having a support port that terminates the base vacuum channel, the support port being defined by an exterior, generally planar surface of the base vacuum channel,
the filtering apparatus and coupling portion having corresponding registration details for forming a registration fit that substantially locks the filtering apparatus to the coupling portion, the registration fit also aligning and abutting the adapter port and the support port generally planar surfaces, the adapter port and abutting support port generally planar surfaces together forming a seal that fluidly connects the adapter vacuum channel with the base vacuum channel.

21. The system as defined by claim 20 wherein the details comprise a protrusion and a corresponding recess.

22. The system as defined by claim 20 wherein the filtering apparatus and base are in registry when oriented in the manner that connects the vacuum channel with the adapter.

23. The system as defined by claim 20 wherein the adapter is upstream of the output receptacle.

24. The system as defined by claim 20 wherein the base has a housing, the base vacuum channel is substantially entirely within the housing.

25. The system as defined by claim 20 wherein the receiving receptacle is an integral part of the adapter.

26. A filtering assembly for use with a substantially rigid base having a base vacuum channel, the assembly comprising:
a receiving receptacle;
an output receptacle; and
an adapter having an adapter body coupled with the receiving and output receptacles and having an adapter port defined by a generally planar surface at the terminal end of an adapter vacuum channel,
the adapter being coupled with the base and having a first registration detail and a second registration detail for orienting the adapter in a manner that connects the base vacuum channel with the adapter port, the registration details substantially locking the adapter to the base to fluidly connect the base vacuum channel and adapter port and suspending the receiving and output receptacles, the first registration detail being spaced from the second registration detail about the body of the adapter to substantially prevent rotation of the adapter when in registry with the base.

27. The filtering assembly as defined by claim 26 wherein the registration detail comprises at least one of a protrusion and a recess.

28. The filtering assembly as defined by claim 26 wherein the base has a plurality of base registration details, the first and second registration details complimentarily mating with at least two of the base registration details while coupled with the base.

29. The filtering assembly as defined by claim 26 further comprising a filter sealed to the receiving receptacle.

30. The assembly as defined by claim 26 wherein the receiving receptacle is an integral part of the adapter.

31. A support base for supporting a filtering apparatus coupled with an output receptacle, the filtering apparatus having a filtering apparatus port, defined by a generally planar surface at the terminal end of a vacuum channel of the filtering apparatus, for receiving a vacuum, the support base comprising:
a substantially rigid housing containing a base vacuum channel terminating at a base vacuum delivery port defined by a generally planar surface; and
a support configured for suspending the filtering apparatus and output receptacle,
the support having a first base registration detail and a second registration detail for orienting the filtering apparatus in a manner that connects the base vacuum channel with the filtering apparatus port, the first and second registration details configured to substantially lock the filtering apparatus to the support to connect the base vacuum channel to the filtering apparatus port while the support supports the filtering apparatus, the first and second registration details substantially preventing rotation of the filtering apparatus when in registry, the first and second registration details being spaced apart on the base, the registration details also abutting the base vacuum delivery port with the filtering apparatus port while substantially locked to fluidly connect the filtering apparatus vacuum channel and the base vacuum channel, the support being upstream of at least a portion of the output receptacle while supporting the filtering apparatus.

32. The base as defined by claim 31 wherein the base registration details comprises one of a protrusion and a recess.

33. The base as defined by claim 31 wherein the vacuum channel is substantially entirely within the housing.

34. The base as defined by claim 31 further including a vacuum receive port for coupling the base vacuum channel with an external vacuum source.

35. A support base for supporting a filtering apparatus coupled with an output receptacle, the filtering apparatus having a filtering port for receiving a vacuum, the filtering port being defined by a generally planar surface at the terminal end of a filtering apparatus vacuum channel, the support base comprising:
a substantially rigid housing substantially entirely containing a base vacuum channel having a base port defined by a generally planar exterior surface at the end of the base vacuum channel, the housing forming a support for removably supporting the filtering apparatus, the support forming an interior containing at least a portion of the base vacuum channel, the base vacuum channel being connected to the filtering port in an abutting relationship of the generally planar surfaces while the support supports the filtering apparatus; and the support being upstream of the output receptacle while the support couples with the filtering apparatus to suspend the output receptacle, wherein the support has a plurality of base registration details for orienting the filtering apparatus in a manner that connects the base vacuum channel with the filtering port.

36. The base as defined by claim 35 further comprising a bottom portion, the output receptacle being spaced from the bottom portion when the support couples with the filtering apparatus.

37. A liquid filtering system comprising:
a filtering apparatus having a receiving receptacle for receiving a fluid and a vacuum channel terminating at a port defined by a generally planar surface;
an output receptacle removably coupled with the filtering apparatus; and
a substantially rigid base having a coupling portion with a base vacuum channel terminating at a base port defined by a generally planar surface, the coupling portion being removably couplable with the filtering apparatus to abut the generally planar surfaces to provide a vacuum to the receiving receptacle, the coupling portion suspending the filtering apparatus and output receptacle while the vacuum is provided to the receiving receptacle and the output receptacle is coupled with the filtering apparatus,
the coupling portion of the base being upstream of the output receptacle.

38. The system as defined by claim 37 wherein the filtering apparatus has a plurality of spaced apart registration details, the base having corresponding registration details for orienting the filtering apparatus in a manner that fluidly connects the vacuum channel with the filtering apparatus, the registration details of the base and filtering apparatus substantially preventing movement of the filtering apparatus when coupled with the base.

* * * * *